United States Patent
Schneider et al.

(10) Patent No.: US 7,722,904 B2
(45) Date of Patent: May 25, 2010

(54) COMPOSITIONS AND METHODS FOR STIMULATING SYNTHESIS OF PRO-COLLAGEN OR COLLAGEN AND HYALURONIC ACID

(75) Inventors: Louise M. Schneider, Rockford, MI (US); Donald J. Pusateri, Hemet, CA (US); Tom Q. La, Murrieta, CA (US)

(73) Assignee: Access Business Group International LLC, Ada, MI (US)

( * ) Notice: Subject to any disclaimer, the term of this patent is extended or adjusted under 35 U.S.C. 154(b) by 31 days.

(21) Appl. No.: 11/982,122

(22) Filed: Nov. 1, 2007

(65) Prior Publication Data

US 2009/0117211 A1 May 7, 2009

(51) Int. Cl.
*A01N 65/22* (2009.01)
*A61K 36/33* (2006.01)

(52) U.S. Cl. .......................................... 424/746; 424/767
(58) Field of Classification Search ........................ None
See application file for complete search history.

(56) References Cited

U.S. PATENT DOCUMENTS

| | | | |
|---|---|---|---|
| 6,361,806 B1 | 3/2002 | Allen | |
| 6,410,048 B1 * | 6/2002 | Fotinos | |
| 6,555,118 B1 | 4/2003 | Niazi | |
| 6,737,086 B2 | 5/2004 | Gutierrez et al. | |
| 2004/0022839 A1 | 2/2004 | Barnikol | |
| 2006/0147397 A1 | 7/2006 | Uehara | |
| 2007/0134355 A1 | 6/2007 | Nöldner et al. | |

FOREIGN PATENT DOCUMENTS

| | | |
|---|---|---|
| WO | WO 2005/120174 A3 | 12/2004 |
| WO | WO 2005/120174 A2 | 12/2005 |
| WO | WO 2007/072178 A1 | 6/2007 |

OTHER PUBLICATIONS

Trombetta, D et al. Phytomedicine (2006), 13: 352-358. Effect of polysaccnarides from Opunta-ficus indica (L.) cladodes on the healing of dermal wounds in the rat.*
International Search Report and the Written Opinion of the International Searching Authority in International Application No. PCT/US2008/80596, dated Dec. 18, 2008, 7 pages.
Galati, et al., Effect of Opuntia ficus-indica (L.) Mill. Cladodes in the Wound-Healing Process, J. Pacd-2003; Jul. 30, 2002; pp. 1-16.
Effect of Polysaccharides from Opuntia ficus-indica (L.) Cladodes on the Healing of Dermal Wounds in the Rat, Copyright 2006 Urban & Fischer Verlag, Trombetta, D et al.

* cited by examiner

*Primary Examiner*—Michele Flood
(74) *Attorney, Agent, or Firm*—Brinks Hofer Gilson & Lione; G. Peter Nichols

(57) ABSTRACT

A method for improving the appearance, texture and/or moisture of skin comprising administering a composition comprising Chia Seed oil, *Opuntia ficus Indica* extract, or both to stimulate collagen or hyaluronic acid synthesis, or decrease Interleukin-1b synthesis, in the skin.

10 Claims, No Drawings

COMPOSITIONS AND METHODS FOR STIMULATING SYNTHESIS OF PRO-COLLAGEN OR COLLAGEN AND HYALURONIC ACID

BACKGROUND

The field of the invention relates to the use of plant and seed extracts for the treatment of skin. In particular, the present invention involves the use of plant and seed extracts, for example, Chia Seed oil and extracts of *Opuntia Ficus Indica*, to increase the synthesis of cell proteins and macromolecules.

Collagen is the most abundant protein in the human body and is the main component of connective tissue. Collagen is found in cartilage, bone, ligaments, tendon, teeth, and skin. Pro-collagen, the pre-processed form of collagen, is assembled in cells, and consists of three polypeptide chains that form a triple helix stabilized by intramolecular bonding. The triple helical pro-collagen molecule is then modified in the cell and is secreted into the extracellular matrix, where it is further processed to a mature form (tropocollagen). Mature collagen molecules then come together to form collagen fibrils, and collagen fibrils come together to form collagen fibers. The resulting collagen fibers have great tensile strength.

Collagen is a critical component of skin, and, as a result of its structure, contributes to the strength, structure and firmness of skin. Loss of collagen in the skin, typically via enzymatic degradation, is a major factor in the causation of skin wrinkling and the aged appearance of the skin.

Hyaluronic acid is a non-sulfated glycosaminoglycan found in connective, epithelial and neural tissue, and is a major component of the cutaneous extracellular matrix. Hyaluronic acid is synthesized by a class of integral membrane proteins and is secreted into the extracellular matrix. Hyaluronic acid is a polymer of repeated disaccharides of D-glucuronic acid and N-acetylglucosamine; this high carbohydrate content makes it a 'sticky molecule', and as a result, it attracts water, therefore contributing to tissue hydration, lubrication, resistance to compression, and cellular function. Hyaluronic acid can be approximately 25,000 disaccharide repeats in length. Hyaluronic acid's hydrating properties result in increased smoothness, softening and decreased lines and wrinkles in the skin. Hyaluronic acid levels decrease due to aging and exposure to ultraviolet radiation, and reduction of hyaluronic acid levels results in the wrinkling of skin.

Interleukin-1b is a cell signaling molecule that is a member of the interleukin 1 cytokine family. It is produced by activated macrophages as a proprotein, and is proteolytically cleaved, resulting in its active form. This cytokine is an important mediator of the inflammatory response. Increased inflammation of the skin causes redness and swelling.

Therefore, skin treatments that act to increase the synthesis of collagen and of hyaluronic acid would be useful for improving the appearance, texture, and moisture of the skin and for maintaining general skin health. Furthermore, reduction of interleukin-1b synthesis in the skin would be desirable in order to improve the appearance of the skin.

BRIEF SUMMARY

A number of factors cause aging of the skin; one of the most important being the degradation of cellular molecules such as collagen and hyaluronic acid. The present invention is a method comprising administering a composition comprising chia seed oil, an extract of *opuntia ficus*, or both to improve the moisture, texture and appearance of the skin by increasing the synthesis of skin proteins, such as collagen, and of macromolecules found in the extracellular matrix of the skin, such as hyaluronic acid. Additionally, the present invention involves the use of Chia Seed Oil and/or a lipophilic extract of *Opuntia Ficus Indica* to decrease the synthesis of Interleukin-1b. Methods of the present invention can include a step of topical administration or of oral administration.

In one example, the invention is a formulation comprising Chia Seed oil. More preferably, the invention is a composition comprising Chia Seed oil and one or more of the following: safflower seed (*Carthamus tinctorius*) oil; Butylated hydroxytoluene (BHT); meadowfoam seed oil; sesame seed (*seamum indicum*) oil; mineral oil; squalane; shea butter (*butyrospermum parkii*) oil; tocopheryl acetate; fragrance; borage oil; or rice bran oil. In another example, the invention is a method of using this composition to stimulate collagen synthesis, to decrease synthesis of Interleukin-1b, or both.

Another example of the invention is a method for increasing collagen synthesis in a skin cell comprising administering a composition comprising Chia Seed oil to the skin cell, wherein the Chia Seed oil increases collagen synthesis in the skin cell.

In an additional example, the invention is a method of improving the appearance, texture, or moisture of skin by administering a formulation comprising Chia Seed oil to the skin, wherein the Chia Seed oil increases collagen synthesis, decreases the synthesis of Interleukin-1b, or both.

A further example of the invention is a method for decreasing Interleukin-1b synthesis in a skin cell comprising administering a composition comprising Chia Seed oil to the skin, wherein the Chia Seed oil decreases Interleukin-1b synthesis in the skin cell.

Another example of the invention is a formulation comprising *Opuntia Ficus Indica* extract.

A further example of the invention is a method for increasing the synthesis of hyaluronic acid in a skin cell comprising administering a composition comprising *Opuntia Ficus Indica* extract to the skin wherein the *Opuntia Ficus Indica* extract increases hyaluronic acid synthesis in the skin cell.

A further example of the invention is a method for increasing synthesis of collagen in a skin cell comprising administering a composition comprising *Opuntia Ficus Indica* extract to the skin, wherein the *Opuntia Ficus Indica* extract increases collagen synthesis in the skin cell.

A further example of the invention is a method for decreasing Interleukin-1b synthesis in a skin cell comprising administering a composition comprising a lipophilic extract of *Opuntia Ficus Indica* to the skin, wherein the *Opuntia Ficus Indica* extract decreases Interleukin-1b synthesis in the skin cell.

An additional example of the invention is a method of improving the appearance, texture, or moisture of skin by administering a formulation comprising *Opuntia Ficus Indica* extract to the skin, wherein the *Opuntia Ficus Indica* extract increases collagen synthesis in the skin, increases hyaluronic acid synthesis in the skin, or both.

An additional example of the invention is a method of improving the appearance, texture, or moisture of skin by administering a formulation comprising a lipophilic *Opuntia Ficus Indica* extract to the skin, wherein the lipophilic *Opuntia Ficus Indica* extract decreases Interleukin-1b synthesis in the skin.

Another example of the invention is a formulation comprising Chia Seed oil and/or *Opuntia Ficus Indica* extract. More preferably, the invention is a composition comprising Chia Seed oil and/or *Opuntia Ficus Indica* extract and one or more of water; polyquaternium-10; methylparaben; Polyethylene glycol (PEG)-8; disodium lauroamphodacetate; sodium trideceth sulfate; hexylene glycol; sodium methyl cocoyl taurate; tea-lauryl sulfate; lauryl betaine; sodium myristoyl sarcosinate; Polyethylene glycol (PEG)-150 distearate; citric acid-anhydrous; sodium citrate-dihydrate; diazolidinyl urea; and fragrance. In a further example, the present invention comprises a method of administering the aforementioned composition to increase collagen and/or hyaluronic acid synthesis in the skin or to decrease IL-1b synthesis in the skin.

An additional example of the present invention is a composition comprising Chia Seed oil and/or *Opuntia Ficus Indica* extract and one or more of water; disodium EDTA; methylparaben; propylparaben; glycerin; polysorbate 60; panthenol; isopropyl palmitate; octyl palmitate; C12-15 alkyl benzoate; dipropylene glycol dibenzoate; PPG-15 stearyl ether benzoate; isododecane; isoeicosane; squalane; shea butter (butylspermum parkii) oil; jojoba oil; dimethicone; glyceryl stearate; PEG-100 stearate; cetyl alcohol; butylene glycol; chlorphenesin; fragrance; polyacrylamide; C13-14 isoparaffin; and Laureth-7. In a further example, the present invention comprises a method of administering the aforementioned composition to increase collagen and/or hyaluronic acid synthesis in the skin or to decrease IL-1 b synthesis in the skin.

Another example of the present invention is a composition comprising Chia Seed oil and/or *Opuntia Ficus Indica* extract and one or more of water; glycerin; aloe vera powder; panthenol; methylparaben; propylparaben; hydroxyethylacrylate; sodium acryloyldimethyl taurate copolymer; polysorbate 60; squalane; behenyl alcohol; cetyl alcohol; tocopheryl acetate; isodecyl neopentanoate; glyceryl trioctanoate; cetearyl alcohol; cetearyl glucoside; dimethicone; butylene glycol; chlorphenesin; chamomilla recutita flower extract; biosaccharide gum-1; pentadecalactone; and dipropylene glycol. In a further example, the present invention comprises a method of administering the aforementioned composition to increase collagen and/or hyaluronic acid synthesis in the skin or to decrease IL-1 b synthesis in the skin.

Another example of the present invention is a composition comprising Chia Seed oil and/or *Opuntia Ficus Indica* extract and one or more of cyclomethicone; polyethylene glycol (PEG)/PPG-18/18 dimethicone; cyclopentasiloxane; disteardimonium hectorite; SD alcohol 40; phenoxyethanol; methylparaben; ethylparaben; propylparaben; trimethylsiloxysilicate; zinc oxide; triethoxycaprylysilane; micronized titanium dioxide; titanium dioxide; iron oxides (yellow; red; black; etc.); caprylysilane; purified water; and sodium chloride. In a further example, the present invention comprises a method of administering the aforementioned composition to increase collagen and/or hyaluronic acid synthesis in the skin or to decrease IL-1b synthesis in the skin.

A further example of the present invention is a composition comprising Chia Seed oil and/or *Opuntia Ficus Indica* extract and one or more of diisopropyl dimer dilinoleate; squalane; cyclomethicone; phenoxyethanol; propylparaben; cyclomethicone; polyethylene glycol (PEG)/PPG-18/18 dimethicone; trimethylsiloxysilicate; cyclopentasiloxane; disteardimonium hectorite; SD alcohol 40; titanium dioxide; aluminum hydroxide; stearic acid; caprylysilane; zinc oxide; triethoxycaprylysilane; iron oxides (yellow; red; black; etc.); polyethelene beads; purified water; sodium chloride; butylene glycol; methylparaben; and glycerin. In a further example, the present invention comprises a method of administering the aforementioned composition to increase collagen and/or hyaluronic acid synthesis in the skin or to decrease IL-1b synthesis in the skin.

Another example of the present invention is a composition comprising Chia Seed oil and/or *Opuntia Ficus Indica* extract and one or more of purified water; C12-15 alkl benzoate; acrylates/C10-30 alkyl acrylate; xanthan gum; methylparaben; butylene glycol; glycerin; sorbitan laurate; panthenol; behenyl alcohol; petrolatum; squalane; isopropyl isostearate; dimethicone; arginine; phenoxyethanol; propylparaben; ethylparaben; and fragrance. In a further example, the present invention comprises a method of administering the aforementioned composition to increase collagen and/or hyaluronic acid synthesis in the skin or to decrease IL-1b synthesis in the skin.

Another example of the present invention is a composition comprising Chia Seed oil and/or *Opuntia Ficus Indica* extract and one or more of purified water; sodium EDTA; glycerin; methylparaben; propylparaben; panthenol; sodium acrylate/acryloyidimethyl taurate copolymer; isohexadecane; polysorbate 80; hydroxyethylacrylate/sodium acryloyldimethyl taurate copolymer; squalane; polysorbate 60; C12-15 alkyl benzoate; dipropylene glycol dibenzoate; PPG-15 stearyl ether benzoate; octinoxate (octyl methoxycinnimate); oxybenzone; dicaprylyl ether; isodecyl neopentanoate; zinc oxide; triethoxycaprylysilane; tocopheryl acetate; cetyl alcohol; behenyl alcohol; petrolatum; cetearyl alcohol; cetearyl glucoside; butylene glycol; chlorphenesin; benzyl alcohol and fragrance. In a further example, the present invention comprises a method of administering the aforementioned composition to increase collagen and/or hyaluronic acid synthesis in the skin or to decrease IL-1 b synthesis in the skin.

A further example of the present invention is a composition comprising Chia Seed oil and/or *Opuntia Ficus Indica* extract and one or more of purified water; disodium EDTA; xanthan gum; glycerin; panthenol; methyl methacrylate crosspolymer; silica; HDI/trimethylol hexyllactone crosspolymer; silica; C12-15 alkyl benzoate; isodecyl neopentanoate; octinoxate (octyl methoxycinnimate); cetearyl alcohol; cocoglucoside; C20-22 alkyl phosphate; C20-22 alcohols; oxybenzone; zinc oxide; triethoxycaprylylsilane; palmitoyl proline; magnesium palmitoyl glutamate; sodium palmitoyl sarcosinate; cyclopentasiloxane; C30-45 alkyl cetearyl crosspolymer; polyacrylate 13; polyisobutene; polysorbate 20; diazolidinyl urea; iodopropynyl butylcarbamate; tocopheryl acetate; and fragrance. In a further example, the present invention comprises a method of administering the aforementioned composition to increase collagen and/or hyaluronic acid synthesis in the skin or to decrease IL-1b synthesis in the skin.

A further example of the present invention is a composition comprising Chia Seed oil and/or *Opuntia Ficus Indica* extract and one or more of purified water; glycerin; disodium EDTA; panthenol; sodium citrate; citric acid; butylene glycol; chlorphenesin; methylparaben; ceteth-20; and fragrance. In a further example, the present invention comprises a method of administering the aforementioned composition to increase collagen and/or hyaluronic acid synthesis in the skin or to decrease IL-1b synthesis in the skin.

A further example of the present invention is a composition comprising Chia Seed oil and/or *Opuntia Ficus Indica* extract and one or more of purified water; sodium magnesium silicate; methyl gluceth-20; dimethly isosorbide; panthenol; silica; SD alcohol 40-B; salicylic acid; methylparaben; chlorphenesin; ceteth-20; fragrance; witch hazel; and glycerin. In a further example, the present invention comprises a method of administering the aforementioned composition to increase collagen and/or hyaluronic acid synthesis in the skin or to decrease IL-1b synthesis in the skin.

Another example of the invention is a method for increasing collagen synthesis in a skin cell comprising administering a composition comprising Chia Seed oil and *Opuntia Ficus Indica* extract to the skin cell, wherein the Chia Seed oil and *Opuntia Ficus Indica* extract increase collagen synthesis in the skin cell.

An additional example of the invention is a method of improving the appearance, texture, or moisture of skin comprising administering a composition of Chia Seed oil and *Opuntia Ficus Indica* extract to the skin, wherein the Chia Seed oil and *Opuntia Ficus Indica* extract increase collagen synthesis, increase hyaluronic acid synthesis or both.

An additional example of the invention is a method of improving the appearance, texture, or moisture of skin by administering a composition Chia Seed oil and a lipophilic *Opuntia Ficus Indica* extract to the skin, wherein the Chia Seed oil and/or *Opuntia Ficus Indica* extract increase collagen synthesis, increase hyaluronic acid synthesis, and/or decrease Interleukin-1b synthesis, or all three.

DETAILED DESCRIPTION

It is to be understood that this invention is not limited to the particular methodology or protocols described herein. Further, unless defined otherwise, all technical and scientific terms used herein have the same meaning as commonly understood to one of ordinary skill in the art to which this invention belongs. It is also to be understood that the terminology used herein is for the purpose of describing particular embodiments only, and is not intended to limit the scope of the present invention, which will be limited only by the claims.

The present invention is based on the surprising effect of unique ingredients on improving skin moisture, texture, and appearance. More specifically, the present invention is a method of using unique ingredients, for example, Chia Seed oil and/or *Opuntia Ficus Indica* extract, to improve skin moisture, texture, and appearance by increasing the synthesis of skin proteins such as collagen, or extracellular macromolecules such as hyaluronic acid.

Chia Seed oil is extracted from Chia Seeds (*Salvia hispanica*). Chia is grown commercially for its seed, a food that is very rich in Omega 3 fatty acids (for example, alpha-linolenic acid). Historically, Chia Seeds served as a staple food of the Aztec cultures of Central Mexico. Chia sprouts are used in a similar manner as alfalfa sprouts in salads, sandwiches and other dishes. Omega 3 is an essential fatty acid (EFA) found in Chia oil. EFA's are essential for regulating healthy skin. EFA's cannot be produced by the human body and must be supplemented via diet, or by direct application. In cosmetics, alpha-linolenic acid shows benefits such as anti-inflammatory and anti-allergic properties.

Although the use of Chia Seed oil in cosmetics and skin creams, and in wound healing has been disclosed (e.g., U.S. Pat. No. 6,497,889 and U.S. Patent Application 2004/0022839), the present invention is based on the surprising discovery that chia seed oil can increase collagen synthesis, and decrease Interleukin-1b synthesis.

The pulp from *Opuntia Ficus Indica* is known to contain carbohydrates like glucose and fructose. Glucose and fructose are humectant type ingredients that help hold moisture in the skin. The pulp from the *Opuntia* leaves has been historically used as an ointment and the young leaf like stems have also been ground and applied as a poultice to allay heat and inflammation. The fruits and young stems of *Opuntia Ficus Indica* are also used as a food source.

Although the use of *Opuntia Ficus Indica* extract for cosmetic and dermatologic applications has been disclosed (e.g., U.S. Pat. No. 6,555,118), the present invention is based on the surprising discovery that *Opuntia Ficus Indica* extract can increase hyaluronic acid synthesis and that a lipophilic extract of *Opuntia Ficus Indica* can decrease Interleukin-1b synthesis.

Although each of the extracts used in the present invention is commercially available, there are numerous extraction methods that can be used to produce an extract to be used in the present invention. Some examples of extraction methods that can be used to produce an extract to be used in the present invention are described below. Other examples are known and described in the art, including in various publications and patents. The extraction methods described more fully below are exemplary and one of ordinary skill in the art will appreciate that other extraction techniques and methods may be used to obtain an extract useful in the present invention. Botanical compounds in particular can be obtained via numerous extraction methods, including maceration/solvent, digestion, percolation, and expression/compression/squeezing. Solvents for extraction can be broadly classified as polar (hydrophilic) or non-polar (lipophilic), and examples of solvents include ethyl alcohol, ether, and acetone. Water also may be used as an extract solvent.

In one example, an extract useful in the unique compositions of the present invention might be obtained using an aqueous solvent extraction technique. More specifically, an extract useful in the present invention, such as *Opuntia Ficus Indica* extract, can be produced by extracting *Opuntia Ficus Indica* pads with an aqueous solvent, for example, water. Other parts of *Opuntia Ficus Indica* plants including the stem, leaves, roots, fruit, rind, etc. may be extracted to yield an *Opuntia Ficus Indica* extract useful in compositions and methods of the present invention.

Total hydro-ethanolic extraction techniques might also be used to obtain an extract useful in the unique compositions of the present invention. Generally, this is referred to as a lump-sum extraction. The extract generated in this process will contain a broad variety of phytochemicals present in the extracted material including fat and water solubles. Following collection of the extract solution, the solvent will be evaporated, resulting in the extract. In one example, *Opuntia Ficus Indica* extract might be extracted using this technique.

Total ethanol extraction may also be used in the present invention. This technique uses ethanol, rather than hydro-ethanol, as the solvent. This extraction technique generates an extract that may include fat soluble and/or lipophilic compounds in addition to water soluble compounds. An extract of *Opuntia Ficus Indica* might be obtained using this technique. An *Opuntia Ficus Indica* extract obtained using this method extraction may be used in compositions and methods of the present invention to decrease Interleukin-1b synthesis.

Another example of an extraction technique that might be used to obtain an extract useful in the present invention is supercritical fluid carbon dioxide extraction (SFE). In this extraction procedure the material to be extracted is not exposed to any organic solvents. Rather, the extraction solvent is carbon dioxide, with or without a modifier, in super-critical conditions (>31.3° C. and >73.8 bar). Those of skill in the art will appreciate that temperature and pressure conditions can be varied to obtain the best yield of extract. This technique generates an extract of fat soluble and/or lipophilic compounds, similar to the total hexane and ethyl acetate extraction technique described above. An *Opuntia Ficus Indica* extract obtained using this method extraction may be used in compositions and methods of the present invention to decrease Interleukin-1b synthesis.

In another example, the extraction of *Opuntia Ficus Indica* extract and Chia Seed oil do not involve ethanol extractions. For example, an *Opuntia Ficus* Indica extract may be obtained by using water at room temperature. A Chia Seed oil useful in the present invention may be obtained through cold pressing of Chia Seeds. The Chia Seeds may be separated from other plant materials prior to the extraction.

Many botanical compounds are also commercially available. Chia Seed oil can be obtained commercially from suppliers such as Green Grown Products, Inc. (http://www.greengrownproducts.com/Chia-Seed-meal-oil.htm#Chiaoil). *Opuntia Ficus Indica* extract can also be commercially obtained from suppliers such as Hangzhou New Asia International Co. Ltd. (http://www.tradekey.com/selloffer_view/id/406281.htm).

Those of skill in the art will appreciate that there are many other extraction processes, both known in the art and described in various patents and publications that can be used to obtain the extracts to be used in practicing the present invention.

FORMULATIONS OF THE PRESENT INVENTION

The formulations of the present invention are designed to offer a combination of ingredients, in addition to the plant or seed extracts. Specifically, formulations of the present invention comprise a unique combination of ingredients that target a number of key molecules involved in skin health, and also modulate cellular activity of skin cells to promote improved skin health. In particular, ingredients comprising the formulations of the present invention stimulate synthesis of collagen and/or hyaluronic acid. For example, Chia Seed oil and *Opuntia Ficus Indica* extract are inducers of collagen synthesis, alone or in combination, and *Opuntia Ficus Indica* is an inducer of hyaluronic acid synthesis, while Chia Seed oil and the lipophilic extract of *Opuntia Ficus Indica* are effective at inhibiting the synthesis of Interleukin-1b.

As used herein, "stimulating collagen synthesis" is used in its broadest sense and refers to the production of collagen, its incorporation into collagen-containing tissue (including, e.g., the synthesis, processing, cross-linking, secretion, and assembly of collagen fibrils) and the presence of healthy collagen-containing tissue. "Stimulating" or "inducing" collagen synthesis, therefore, refers to the ability of a formulation described herein to positively affect the production of collagen. Stimulating collagen synthesis may be brought about by the ability of the formulations described herein to promote steps, such as biochemical steps, leading to the formation of collagen fibrils.

As used herein, "stimulating hyaluronic acid synthesis" is used in its broadest sense and refers to the production of hyaluronic acid, its incorporation into hyaluronic acid-containing tissue (including, e.g., the synthesis, secretion, processing, and assembly of hyaluronic acid molecules) and the presence of healthy hyaluronic acid-containing tissue. "Stimulating" or "inducing" hyaluronic acid synthesis, therefore, refers to the ability of a formulation described herein to positively affect the production of hyaluronic acid. Stimulating hyaluronic acid synthesis may be brought about by the ability of the formulations described herein to promote steps, such as biochemical steps, leading to the formation of hyaluronic acid molecules.

As used herein "decreasing Interleukin-1b synthesis" is used in its broadest sense and refers to the production of Interleukin-1b in the skin. "Decreasing" or "reducing" Interleukin-1b, therefore, refers to the ability of a formulation described herein to inhibit the production of Interleukin-1b in the skin. Decreasing Interleukin-1b synthesis may be brought about by the ability of the formulations described herein to promote steps, such as biochemical steps, leading to the decrease or inhibition of Interleukin-1b synthesis in the skin.

In one example of the present invention, the formulation comprises the approximately 0.001-30% Chia Seed oil and approximately 0.01-15% *Opuntia Ficus Indica* extract.

In another example of the present invention, the formulation comprises approximately 0.001-30% Chia Seed oil. More preferably, the range of Chia Seed oil is approximately 1-5%.

In a further example of the present invention, the formulation comprises approximately 0.01-15% *Opuntia Ficus Indica* extract. More preferably, the range of *Opuntia Ficus Indica* extract is approximately 0.5 to 3.0%

Methods of Administration

Improved skin appearance, texture, and moisture can be achieved by administering the formulations of the present invention externally, internally, or some combination thereof. Preferably, the formulations of the present invention are administered with an acceptable carrier. For example, the formulation of the present invention could be externally administered with an acceptable carrier in the form of a gel, lotion, cream, tonic, emulsion, etc. As a further example, the formulation of the present invention could be internally administered with an acceptable carrier in the form of a pill, tablet, powder, bar, beverage, etc. Thus, the formulations described herein are useful in a wide variety of finished products, including pharmaceutical products, food products, and beverage compositions. Preferably, the products are useful for providing mammalian skin with an improved texture, appearance, and increased moisture.

When the formulations of the present invention are orally administered in the form of a liquid, the liquid may be water-based, milk-based, tea-based, fruit juice-based, or some combination thereof. Solid and liquid formulations for internal administration according to the present invention can further comprise thickeners, including xanthan gum, carboxymethyl-cellulose, carboxyethylcellulose, hydroxypropylcellulose, methylcellulose, microcrystalline cellulose, starches, dextrins, fermented whey, tofu, maltodextrins, polyols, including sugar alcohols (e.g., sorbitol and mannitol), carbohydrates (e.g. lactose), propylene glycol alginate, gellan gum, guar, pectin, tragacanth gum, gum acacia, locust bean gum, gum arabic, gelatin, as well as mixtures of these thickeners. These thickeners are typically included in the formulations of the present invention at levels up to about 0.1%, depending on the particular thickener involved and the viscosity effects desired.

The solid and liquid (food and beverage) formulations of the present invention can, and typically will, contain an effective amount of one or more sweeteners, including carbohydrate sweeteners and natural and/or artificial no/low calorie sweeteners. The amount of the sweetener used in the formulations of the present invention will vary, but typically depends on the type of sweetener used and the sweetness intensity desired.

In another example, the formulations of the present invention are topically administered in the form of a: solution, gel, lotion, cream, ointment, oil-in-water emulsion, water-in-oil emulsion, stick, spray, paste, mousse, tonic, foundation, or other cosmetically and topically suitable form.

Preferably, formulations of the present invention that are suitable for topical administration are mixed with an acceptable carrier. An acceptable carrier may act variously as solvent, carrier, diluent or dispersant for the constituents of the composition, and allows for the uniform application of the constituents to the surface of the skin at an appropriate dilution. The acceptable carrier may also facilitate penetration of the composition into the skin.

In one example of a formulation for topical application, the acceptable carrier forms from about 70% to about 99.99% by weight of the total composition. In other examples, the acceptable carrier will form from about 85% to 99.99% by weight of the total composition. The acceptable carrier may also form from about 90% to about 99.99% by weight of the total composition; or from about 99.95% to about 99.999% by weight of the total composition. The acceptable carrier can, in the absence of other cosmetic adjuncts or additives, form the balance of the composition.

The various ingredients used in practicing the present invention may be soluble or insoluble in the acceptable carrier. If all ingredients of a formulation are soluble in the acceptable carrier, then the vehicle acts as solvent. However, if all or some ingredients of a formulation are insoluble in the acceptable carrier, then those ingredients are dispersed in the vehicle by means of, for example, a suspension, emulsion, gel, cream or paste, and the like.

Thus, it will be apparent to the skilled artisan that the range of possible acceptable carriers is very broad. For example, acceptable carriers can be emulsions, lotions, creams, or tonics. Acceptable carriers can comprise water, ethanol, butylene glycol, or other various solvents that aid in penetration of the skin. Some examples of suitable vehicles are described in U.S. Pat. Nos. 6,184,247 and 6,579,516, the entire contents of which are incorporated herein by reference.

Preferably the acceptable carrier used in practicing the present invention comprises water and ethanol. Optionally, the acceptable carrier also contains butylene glycol. For example, the acceptable carrier can comprise 2-5% butylene glycol by weight of the composition. In practicing the present invention, preferably this acceptable carrier is mixed with a formulation of the present invention comprising 2% by weight of the total composition. In other examples, the acceptable carrier is mixed with a formulation of the present invention comprising 0.001% to 30% by weight of the total composition; 1% to 5% by weight of the total composition; 0.01% to 15% by weight of the total composition; or 0.5% to 1.0% by weight of the total composition.

In general, however, acceptable carriers according to the present invention may comprise, but are not limited to comprising, any of the following examples: water; castor oil; ethylene glycol monobutyl ether; diethylene glycol monoethyl ether; corn oil; dimethyl sulfoxide; ethylene glycol; isopropanol; soybean oil; glycerin; soluble collagen; safflower seed oil; meadowfoam seed oil; mineral oil; squalene; shea butter; borage oil; or rice bran oil; polyquaternium-10; methylparaben; PEG-8; disodium lauroamphodacetate; sodium trideceth sulfate; hexylene glycol; sodium methyl cocoyl taurate; tea-lauryl sulfate; lauryl betaine; sodium myristoyl sarcosinate; PEG-150 distearate; citric acid-anhydrous; sodium citrate-dihydrate; diazolidinyl urea; disodium EDTA; propylparaben; polysorbate 60; isopropyl palmitate; octyl palmitate; C12-15 alkyl benzoate; dipropylene glycol dibenzoate; PPG-15 stearyl ether benzoate; isododecane; isoeicosane; squalane; jojoba oil; dimethicone; glyceryl stearate; PEG-100 stearate; cetyl alcohol; butylene glycol; chlorphenesin; fragrance; polyacrylamide; C13-14 isoparaffin; Laureth-7; aloe vera powder; aloe vera gel, hydroxyethylacrylate; sodium acryloyldimethyl taurate copolymer; behenyl alcohol; tocopheryl acetate; isodecyl neopentanoate; glyceryl trioctanoate; cetearyl alcohol; cetearyl glucoside; chamomilla recutita flower extract; biosaccharide gum-1; pentadecalactone; dipropylene glycol; cyclomethicone; PEG/PPG-18/18 Dimethicone; cyclopentasiloxane; disteardimonium hectorite; SD alcohol 40; phenoxyethanol; ethylparaben; trimethylsiloxysilicate; triethoxycaprylysilane; micronized titanium dioxide; titanium dioxide; zinc oxide; iron oxides (yellow; red; black; etc.); caprylysilane; sodium chloride; diisopropyl dimer dilinoleate; aluminum hydroxide; stearic acid; polyethelene beads; C12-15 alkly benzoate; acrylates/C10-30 alkyl acrylate; xanthan gum; sorbitan laurate; panthenol; petrolatum; isopropyl isostearate; dimethicone; arginine; phenoxyethanol; acryloyldimethyl taurate copolymer; isohexadecane; polysorbate 80; hydroxyethylacrylate; sodium acryloyldimethyl taurate copolymer; octinoxate (octyl methoxycinnimate); oxybenzone; dicaprylyl ether; isodecyl neopentanoate; cetearyl alcohol; cetearyl glucoside; benzyl alcohol; HDI/trimethylol hexyllactone crosspolymer; silica; isodecyl neopentanoate; coco-glucoside; C20-22 alkyl phosphate; C20-22 alcohols; palmitoyl proline; magnesium palmitoyl glutamate; sodium palmitoyl sarcosinate; C30-45 alkyl cetearyl crosspolymer; polyacrylate 13; polyisobutene; polysorbate 20; iodopropynyl butylcarbamate; sodium magnesium silicate; methyl gluceth-20; dimethly isosorbide; silica; SD alcohol 40-B; salicylic acid; ceteth-20; fragrance; or witch hazel.

Additionally, acceptable carriers used in the present invention may optionally comprise one or more humectants, including but not limited to: dibutyl phthalate; soluble collagen; sorbitol; or sodium 2-pyrrolidone-5-carboxylate. Other examples of humectants that may be used in practicing the present invention can be found in the CFTA Cosmetic Ingredient Handbook, the relevant portions of which are incorporated herein by reference.

Additionally, acceptable carriers in the present invention may optionally comprise one or more emollients including but not limited to: butane-1,3-diol; cetyl palmitate; dimethylpolysiloxane; glyceryl monoricinoleate; glyceryl monostearate; isobutyl palmitate; isocetyl stearate; isopropyl palmitate; isopropyl stearate; butyl stearate; isopropyl laurate; hexyl laurate; decyl oleate; isopropyl myristate; lauryl lactate; octadecan-2-ol; caprylic triglyceride; capric triglyceride; polyethylene glycol; propane-1,2-diol; triethylene glycol; sesame oil; coconut oil; safflower oil; isoamyl laurate; nonoxynol-9; panthenol; hydrogenated vegetable oil; tocopheryl acetate; tocopheryl linoleate; allantoin; propylene glycol; arachis oil; castor oil; isostearic acid; palmitic acid; isopropyl linoleate; lauryl lactate; myristyl lactate; decyl oleate; or myristyl myristate. Other examples of emollients that may be used in practicing the present invention can be found in the CFTA Cosmetic Ingredient Handbook, the relevant portions of which are incorporated herein by reference.

Additionally, acceptable carriers used in the present invention may optionally comprise one or more penetration enhancers including but not limited to: pyrrolidones, for example 2-pyrrolidone; alcohols, such as ethanol; alkanols, such as decanol; glycols, such as propylene glycol, dipropylene glycol, butylene glycol; surfactants; or terpenes.

Other acceptable carriers that may be used in practicing the present invention will be apparent to those of skill in the art and are included within the scope of the present invention.

For example, an acceptable carrier can be a lotion that is topically applied. The lotion may comprise cabomer 981, water, glycerin, isopropyl myristate, mineral oil, shea butter, stearic acid, glycol stearate, cetyl alcohol, dimethicone, preservatives, tea, and various ingredients of the formulations of the present invention.

The formulations of the present invention may also contain various known and conventional cosmetic adjuvants so long as they do not detrimentally affect the desired skin improvement and moisturizing effects provided by the formulation. For example, a formulation of the present invention can further include one or more additives or other optional ingredients well known in the art, which can include but are not limited to fillers (e.g., solid, semi-solid, liquid, etc.); carriers; diluents; thickening agents; gelling agents; vitamins, retinoids, and retinols (e.g., vitamin $B_3$, vitamin A, etc.); pigments; fragrances; sunscreens and sunblocks; anti-oxidants and radical scavengers; organic hydroxy acids; exfoliants; skin conditioners; moisturizers; ceramides, pseudoceramides, phospholipids, sphingolipids, cholesterol, glucosamine, pharmaceutically acceptable penetrating agents (e.g., n-decylmethyl sulfoxide, lecithin organogels, tyrosine, lysine, etc.); preservatives; antimicrobial agents; amino acids such as proline, pyrrolidone carboxylic acid, its derivatives and salts, saccharide isomerate, panthenol, buffers together with a base such as triethanolamine or sodium hydroxide; waxes, such as beeswax, ozokerite wax, paraffin wax; plant extracts, such as Aloe Vera, cornflower, witch hazel, elderflower, or cucumber and combinations thereof. Other suitable additives and/or adjuncts are described in U.S. Pat. No. 6,184,247, the entire contents of which are incorporated herein by reference.

The formulation can include additional inactive ingredients, including, but not limited to surfactants, co-solvents, and excipients. Surfactants, such as hydrophilic and hydrophobic surfactants, can be included in the formulations. Particular surfactants can be used based on the on the overall composition of the formulation and the intended delivery of the formulation. Useful surfactants include polyethoxylated (PEG) fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, polysaccharide esters, polyethylene glycol alkyl phenols, polyoxyethylene-polyoxypropylene block copolymers, sorbitan fatty acid esters, lower alcohol fatty acid esters, ionic surfactants, and mixtures thereof.

The formulations can also include co-solvents such as alcohols and polyols, polyethylene glycols ethers, amides, esters, other suitable co-solvents, and mixtures thereof. The formulations can also include excipients or additives such as sweeteners, flavorants, colorants, antioxidants, preservatives, chelating agents, viscomodulators, tonicifiers, odorants, opacifiers, suspending agents, binders, and mixtures thereof.

Generally, the formulations of the present invention are topically or orally administered at least on a daily basis for a period of time sufficient to bring about the desired level of improvement in skin appearance, texture, and moisture. Topical application or oral administration of the formulations of the invention may continue for any suitable period of time. More specifically, within a few hours to within a few days of the initial application or ingestion, a user may notice the skin has an improved appearance, texture, and moisture. It should be appreciated that the frequency with which the formulations of the present invention should be applied or ingested will vary depending on the desired level improved appearance, texture, and moisture. In particular, the degree of cosmetic enhancement will vary directly with the total amount of composition used.

Useful dosage forms can be prepared by methods and techniques that will be well understood by those of skill in the art and may include the use of additional ingredients in producing tablets, capsules, or liquid dosage forms.

It is intended that the foregoing detailed description be regarded as illustrative rather than limiting. The present invention is further illustrated by the following experimental investigations and examples, which should not be construed as limiting. The contents of all references, patents and published applications cited throughout this patent are hereby incorporated by reference herein.

EXAMPLES

Example 1

Stimulation of Pro-Collagen Synthesis Using Ingredients of the Present Invention Hs27, a human fibroblast cell culture and HEK, a human keratinocyte cell culture, were established in 96 well plates. The cells were exposed to various ingredients of the formulations of the present invention at concentrations of 1 ug/ml-10 ug/ml. The co-cultures were then incubated overnight. The following day supernatants were collected. The supernatants were analyzed for the presence of pro-collagen, a soluble precursor of collagen formed by fibroblasts in the process of collagen synthesis. Pro-collagen synthesis was assayed using commercially available ELISA kits. See e.g., Hasan A, Murata H, Falabella A, Ochoa S, Zhou L, Badiavas E, Falanga V. "Dermal fibroblasts from venous ulcers are unresponsive to the action of transforming growth factor-beta 1." *J Dermatol Sci.* 1997. 16(1):59-66, the entire contents of which are incorporated herein by reference. Takara EIA Kit (http://catalog.takara-bio.co.jp/en/product/manual_info.asp?unitid=U100005420).

Table 1, shown below, illustrates the effect of Chia Seed oil and *Opuntia Ficus Indica* extract on collagen synthesis. The data are expressed as % control collagen from untreated control cells. Table 1 shows that when used alone, Chia Seed oil and *Opuntia Ficus Indica* extract are inducers of collagen synthesis.

TABLE 1

Stimulation of Pro-collagen Synthesis

| Ingredient: | Amount administered: | % Change in Procollagen synthesis relative to control |
|---|---|---|
| Chia Seed Oil | 1 ug/ml | 142% |
| *Opuntia Ficus Indica* extract (hydrophilic) | 1 ug/ml | 176% |

As illustrated in Table 1, Chia Seed oil and *Opuntia Ficus Indica* extract were the potent stimulators of pro-collagen synthesis in fibroblast/keratinocyte co-cultures.

Example 2

Stimulation of Hyaluronic Acid Synthesis Using Ingredients of the Present Invention Hs27, a human fibroblast cell culture and HEK, a human keratinocyte cell culture, were established in 96 well plates.

The cells were exposed to *Opuntia Ficus Indica* extract at concentrations of 1 ug/ml. The co-cultures were then incubated overnight. The following day supernatants were collected. The supernatants were analyzed for the presence of hyaluronic acid. Hyaluronic acid synthesis was assayed using commercially available ELISA kits. The protocol for this procedure is explained more fully by Lindqvist U., Chichibu K., Delpech B., Goldberg R L, Knudson W., Poole A R, Laurent T C. 1992. "Seven different assays of hyaluronan compared for clinical utility." *Clin. Chem.* 38(1):127-32, the entire contents of which are hereby incorporated by reference.

Table 2, shown below, illustrates the effect of *Opuntia Ficus Indica* extract on hyaluronic acid synthesis. The data are expressed as % control hyaluronic acid from untreated control cells. Table 2 shows that *Opuntia Ficus Indica* extract is a potent inducer of Hyaluronic Acid synthesis.

TABLE 2

Stimulation of Hyaluronic acid Synthesis

| Ingredient: | Amount administered: | % Change in Hyaluronic Acid synthesis relative to control |
|---|---|---|
| *Opuntia Ficus Indica* Extract | 1 μg/ml | 143% |

As illustrated in Table 2, *Opuntia Ficus Indica* extract induced higher levels of hyaluronic acid synthesis than the untreated control cells.

Example 3

Inhibition of Interleukin-1b Synthesis Using Ingredients of the Present Invention Hs27, a human fibroblast cell culture and HEK, a human keratinocyte cell culture, were established in 96 well plates. The cells were exposed to Chia Seed oil at concentrations of 100 ug/ml. The co-cultures were then incubated overnight. The following day supernatants were collected. The supernatants were analyzed for the presence of Interleukin-1b. Interleukin-1b synthesis was assayed using commercially available ELISA kits. The protocol for this procedure is explained more fully by Allen-Hall L, Cano P, Arnason J T, Rojas R, Lock O, Lafrenie R M. Treatment of THP-1 cells with *Uncaria tomentosa* extracts differentially regulates the expression if IL-1 beta and TNF-alpha. J Ethnopharmacol. 2007 Jan. 19; 109(2): 312-7, the entire contents of which are hereby incorporated by reference.

Table 3 shows the effect of Chia Seed oil and a lipophilic extract of *Opuntia Ficus Indica* on Interleukin-1b synthesis. The data are expressed as % control Interleukin-1b from untreated control cells. Table 3 shows that Chia Seed oil and a lipophilic extract of *Opuntia Ficus Indica* reduced Interleukin-1b synthesis.

TABLE 3

Effects of Chia Seed Oil and Lipophilic *Opuntia ficus Indica* extract on Interleukin-1b Synthesis

| Ingredient | Amount | % Decrease Interleukin-1b Synthesis relative to control |
|---|---|---|
| Chia Seed Oil | 100 ug/ml | 80% |
| *Opuntia Ficus Indica* Extract (lipophilic) | 100 ug/ml | 85% |

As illustrated in Table 3, when used alone, Chia Seed Oil and a lipophilic extract of *Opuntia Ficus Indica* reduced levels of Interleukin-1b synthesis compared with untreated control cells.

The invention claimed is:

1. A method for increasing collagen synthesis in a skin cell comprising administering an effective amount of a composition comprising Chia seed (*Salvia hispanica*) oil present at a concentration of about 0.001 to about 30% by weight of the composition to the skin cell, wherein the Chia seed (*Salvia hispanica*) oil induces collagen synthesis.

2. The method in claim 1, wherein the Chia Seed (*Salvia hispanica*) oil is topically administered in the form of a gel, lotion, cream, ointment, emulsion, paste or mousse.

3. The method of claim 1, wherein the Chia Seed (*Salvia hispanica*) oil is present at a concentration of about 1-5% by weight of the composition.

4. The method of claim 1, wherein the composition further a concentration of an *Opuntia Ficus Indica* extract.

5. The method of claim 4, wherein the concentration of the *Opuntia Ficus Indica* extract is about 0.01-15% by weight of the composition.

6. The method of claim 5, wherein the concentration of the *Opuntia Ficus Indica* extract is about 0.05-3% by weight of the composition.

7. A method for increasing collagen synthesis in a skin cell comprising administering an effective amount of a composition comprising Chia seed (*Salvia hispanica*) oil present at a concentration of about 0.001% to about 30% by weight of the composition and a concentration of an *Opuntia Ficus Indica* extract to the skin cell, wherein the composition increases collagen synthesis and hyaluronic acid synthesis.

8. The method of claim 7, wherein the Chia seed (*Salvia hispanica*) oil is present at a concentration of about 0.001-30% by weight of the composition and the *Opuntia Ficus Indica* extract is present at a concentration of about 0.01-15% by weight of the composition.

9. The method of claim 7, wherein the Chia seed (*Salvia hispanica*) oil is present at a concentration of about 1-5% by weight of the composition.

10. The method of claim 7, wherein the *Opuntia Ficus Indica* extract is present at a concentration of about 0.05-3% by weight of the composition.

\* \* \* \* \*

UNITED STATES PATENT AND TRADEMARK OFFICE
CERTIFICATE OF CORRECTION

PATENT NO. : 7,722,904 B2  Page 1 of 1
APPLICATION NO. : 11/982122
DATED : May 25, 2010
INVENTOR(S) : Louise M. Schneider et al.

It is certified that error appears in the above-identified patent and that said Letters Patent is hereby corrected as shown below:

In the Claims

In column 14, claim 4, around line 30, after "the composition further" insert --comprises--.

Signed and Sealed this

Seventeenth Day of August, 2010

David J. Kappos
*Director of the United States Patent and Trademark Office*